(12) United States Patent
Yang

(10) Patent No.: US 6,255,543 B1
(45) Date of Patent: Jul. 3, 2001

(54) PARTIALLY FLUORINATED POLYMERS

(75) Inventor: Zhen-Yu Yang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/730,434

(22) Filed: Dec. 5, 2000

Related U.S. Application Data

(62) Division of application No. 09/194,282, filed as application No. PCT/US97/09121 on May 27, 1997.
(60) Provisional application No. 60/018,493, filed on May 28, 1996.

(51) Int. Cl.[7] ........................ C07C 21/18; C07C 21/02; C07C 21/19

(52) U.S. Cl. ................... 570/135; 570/123; 570/134; 570/136; 570/153

(58) Field of Search ..................... 570/135, 134, 570/153, 123, 136

(56) References Cited

U.S. PATENT DOCUMENTS 5,475,071 * 12/1995 Smart ............................. 526/252
5,557,018 * 9/1996 Smart ............................. 570/135

* cited by examiner

*Primary Examiner*—Fred Zitomer

(57) ABSTRACT

Selected novel partially fluorinated α,ω-dienes can be free radically (co)polymerized to form polymers in which cyclic structures are present. The polymers are useful for films, coatings and molded parts.

3 Claims, No Drawings

PARTIALLY FLUORINATED POLYMERS

This application is a Division of Ser. No. 09/194,282 Nov. 23, 1998 which is a 317 of PCT/US97/0921 May 27, 1997 and claims benefit of Ser. No. 60/018,493 May 28, 1996.

FIELD OF THE INVENTION

This invention concerns polymers made from selected partially fluorinated dienes, in which the repeat units are cycloaliphatic. Also disclosed are novel monomers for making these polymers.

TECHNICAL BACKGROUND

Free radical polymerizations which include nonconjugated dienes (and bis vinyl ethers) usually yield polymers which are crosslinked because of the "separate" reaction of each of the double bonds with the free radicals in the reactions. However, it is known that in some instances perfluorinated or partially fluorinated compounds containing two such double bonds do not form crosslinked polymers, but form polymers containing cyclic structures.

U.S. Pat. Nos. 5,326,917, 5,313,003, 5,260,492, 4,897,457, J. E. Fearn, et al., J. Polym. Sci. A-1, vol. 4, p. 131–140 (1966) and D. W. Brown, et al., J. Polym. Sci. A-2, vol. 7, p. 601–608 (1969) all describe the polymerization of partially or fully fluorinated compounds containing two double bonds which give polymers having cyclic structures. The instant monomers and polymers are not disclosed therein.

D. J. Burton, et al., J. Fluorine Chem., vol. 50, p. 257–264 (1990) describe the synthesis of 1,1,2,3,3-pentafluoro-1,5-heaxdiene. No homologs are described.

SUMMARY OF THE INVENTION

This invention concerns a polymer, comprising, one or more of the repeat units

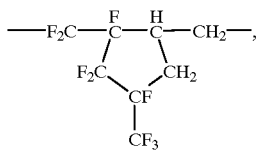
(IA)

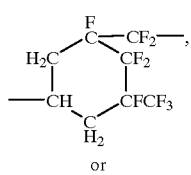
(IB)

or

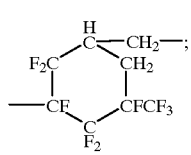
(IC)

or one or more of the repeat units

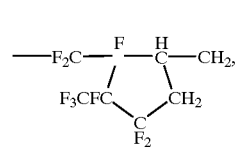
(IIA)

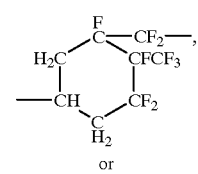
(IIB)

or

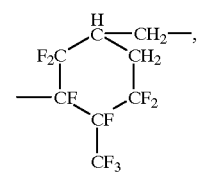
(IIC)

or both.

This invention also concerns a compound of the formula $CF_2=CFCF_2CF(CF_3)CH_2CH=CH_2$ or $CF_2=CFCF(CF_3)CF_2CH_2CH=CH_2$.

DETAILS OF THE INVENTION

The compounds $CF_2=CFCF_2CF(CF_3)CH_2CH=CH_2$ or $CF_2=CFCF(CF_3)CF_2CH_2CH=CH_2$ can be free radically polymerized to polymers containing one or more cyclic structures. When the monomer is $CF_2=CFCF_2CF(CF_3)CH_2CH=CH_2$, a polymer with one or more of the repeat units (IA), (IB), and (IC) is produced. When the monomer is $CF_2=CFCF(CF_3)CF_2CH_2CH=CH_2$, a polymer with one or more of the repeat units (IIA), (IIB) and (IIC) is produced. The synthesis of these two monomers is described in Examples 1–3. These 2 compounds may be separated from their mixture by methods known in the art, such as gas chromatography or liquid phase chromatography.

These monomers may be polymerized by themselves to form homopolymers, or copolymerized with other monomers to form copolymers. By "comprising" in describing these polymers is meant that they contain the above cyclic repeat units, plus any other repeat units from other monomers. Suitable comonomers include fluorinated and unfluorinated compounds such as tetrafluoroethylene, hexafluoropropylene, vinylidene fluoride, perfluoro(methyl vinyl ether), perfluoro(propyl vinyl ether), methyl vinyl ether, propylene, ethylene, chlorotrifluoroethylene, and perfluoro(2,2-dimethyl-1,3-dioxole). Preferred comonomers are tetrafluoroethylene, perfluoro(propyl vinyl ether) and perfluoro(2,2-dimethyl-1,3-dioxole), and tetrafluoroethylene is especially preferred.

The homo- and copolymers described herein are useful for films, coatings, and for molded articles. Such items can be made by standard techniques. Since these polymers are at least partially fluorinated, they have superior chemical resistance, and in many cases superior thermal properties.

The polymerizations described herein may be done by methods well known to the artisan, see for instance polymerizations methods described in H. Mark, et al., Ed., Encyclopedia of Polymer Science and Engineering, vol. 16, John Wiley & Sons, New York, 1989, p. 577–648. The polymerizations may be done neat, in aqueous emulsion or suspension, in solution or organic suspension. They may be done in batch, semibatch or continuous operations. A free radical polymerization initiator is used, suitable initiators including peroxides such as perfluoro(propionyl peroxide) (3P), azonitriles such as azobis(isobutyIronitrile) (AIBN), and redox initiators such as persulfate-bisulfite. As is well known, the process is run at a temperature at which the initiator generates free radicals.

In the Examples, the following abbreviations are used:
AIBN—azobis(isobutyronitrile)
CFC-122—1,1,2-trichloro-1,2,2-trifluoroethane
DSC—differential scanning calorimetry
DMF—N,N-dimethylfonnamide
PDD—perfluoro(2,2-dimethyl-1,3-dioxole)
TGA—thermogravimetric analysis Glass transition temperatures were taken as the beginning of the transition, while melting points were taken as the peak of the melting endotherm. The heating rate for the DSC was 20° C./min.

EXAMPLE 1

Preparation of $ClCF_2ClCFCF_2CFICF_3$ and $CF_2ClCFClCF(CF_3)CF_2I$

A mixture of 280 g of $CF_2ClCFClI$ and 400 g of $CF_3CF=CF_2$ was heated in a autoclave at 200° C. for 15 hours. The reaction mixture (367.4 g) was distilled on a 91 cm spinning band column to give 19 g of bp 64 to 98° C., 99.2 g of $CF_2ClCFClI$, bp 99 to 101° C., 8.5 g of bp 61° C./5.3 kPa to 75° C./5.3 kPa and 199 g of $CF_2ClCFClCF_2CFICF_3$ and $CF_2ClCFClCF(CF_3)CF_2I$ in a 94 to 6, bp 75° C./5.3 kPa. $^{19}F$ NMR for major product: −62.0 to −64.8 (m, 2F), −72.5 (m, −72.9 (m) (total 3F), −99.6 (m), −101.0 (dm, J=275 Hz), −105.1 (dm, J=275 Hz) (total 2F), −125.7 (m), −129.0 (m), (total 1F), −138.5 (m), −142.8 (m) (total 1F).

HRMS: calcd for $C_5F_9Cl_2I$: 427.8278. Found: 427.8272.

EXAMPLE 2

Preparation of $CF_2ClCFClCFCF_3CH_2CHICH_2OAc$ and $CF_2ClCFClCF(CF_3)CF_2CH_2CHICH_2OAc$ A mixture 20 g of allyl acetate 43 g of a mixture $CF_2ClCFClCF_2CFICF_3$ and $CF_2ClCFClCF(CF_3)CF_2I$ in a 94 to 6, 1.5 g of copper powder and 60 mL of exane was stirred at 72° C. overnight. After removal of solids, the filtrate was evaporated to give 63.2 g of residue, which was distilled to give 26.7 g of 1 to 1 adducts, bp 80° C./12 Pa. IR: 1752 (s), 1229 (s), 1169 (s), 1047 (s). HRMS: calcd for $C_{10}H_8O_2F_9Cl_2$—I: 400.9756. Found: 400.9705.

EXAMPLE 3

Preparation of $CF_2=CFCF_2CF(CF_3)CH_2CH=CH_2$ and $CF_2=CFCF(CF_3)CF_2CH_2CH=CH_2$ To a stirred solution of 9.0 g of Zn and 30 mL of DMF was slowly added 24 g of 1 to 1 adducts of Example 2 at 80° C. After the resulting mixture was stirred at 80° C. for 5 hours, volatiles were distilled out and collected in a −78° C. receiver at 1.3 kPa. The distillate was washed with water, NaCl solution and dried over $MgSO_4$ and redistilled to give 9.8 g of product, bp 102–103° C.

$^{19}F$ NMR: −91.0 (ddt, J=53.8 Hz, J=38.0 Hz, J=5.9 Hz, 1F), −75.6 (m, 3F), −106.2 (ddtd, J=116.0 Hz, J=53.8 Hz, J=27.4 Hz, J=5.8 Hz, 1F), −113.5 (dm, J=27.4 Hz, 2F), −180.9 (m, 1F), −186.2 (dm, J=116.0 Hz, 1F). $^1H$ NMR: 5.80 (m, 1H), 5.30 (m, 2H), 2.85 (m, 2H). IR: 3043 (w), 1789.0 (s), 1652 (w), 1366 (s), 1316 (s), 1221 (s), 1193 (s). HRMS: calcd for $C_8H_5F_9$: 272.0247. Found: 272.0239.

EXAMPLE 4

Homopolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ Initiated by Bis(perfluoropropionyl) Peroxide A 25 mL glass ampul fitted with a Teflon® coated stir bar was charged with 0.01 mL of 5% of bis(perfluoropropionyl) peroxide in 1,1,2-trichloro-trifluoroethane and 0.71 g of the title compounds. The ampul was sealed and cooled in a liquid nitrogen bath. After being evacuated and purged with $N_2$ alternately six times, contents of the sealed ampul were stirred at 40° C. for 4 hours. The white heterogeneous mixture was filtered and washed with ethyl acetate and dried under vacuum at 100° C. to give 0.50 g of polymer.

The IR spectrum of this polymer showed no absorption at around 1790 and 1650 $cm^{31\ 1}$ which could be attributed to double bonds in the polymer. This polymer was insoluble in acetone, ethyl acetate, DMF and hexafluorobenzene. The polymer had a glass transition temperature of 130° C., and no melting point by DSC (second heat). By TGA the polymer showed a 10% weight loss temperature of about 430° C. in nitrogen and 400° C. in air, respectively, when heated at 20° C./minute.

EXAMPLE 5

Homopolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ Initiated by Initiated by AIBN A glass ampul fitted with a Teflon® coated stir bar was charged with 7 mg of AIBN, 0.72 g of the title compound. The ampul was sealed and cooled in a liquid nitrogen bath. After being evacuated and purged with $N_2$ alternately six times, contents of the sealed ampul were stirred at 75° C. for 48 hours. The white heterogeneous solution were filtered and washed with CFC113 and dried under vacuum at 110° C. to give 0.35 g of polymer.

This polymer was insoluble in acetone, ethyl acetate, DMF and hexafluorobenzene. The polymer had a glass transition temperature of 130° C., and no melting point by DSC (second heat). By TGA the polymer showed a 10% weight loss temperature of about 430° C. in nitrogen and 400° C. in air, respectively, when heated at 20° C./minute.

EXAMPLE 6

Copolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ with Perfluoropropyl Vinyl Ether (PPVE)

A 25 mL glass ampul fitted with a Teflon® coated stir bar was charged with 0.01 mL of 5% of bis(perfluoropropionyl) peroxide in 1,1,2-trichlorotrifluoroethane, 0.71 g of the title compounds and 0.71 g of PPVE. The ampul was sealed and cooled in a liquid nitrogen bath. After being evacuated and purged with $N_2$ gas six times, contents of the sealed ampul were stirred at 40° C. overnight. The white solid was washed with methanol and dried under vacuum at 100° C. to give 0.50 g of polymer. The polymer had a glass transition temperature of 131.6° C. and no melting point by DSC (second heat). By TGA the polymer showed a 10% weight loss temperature of about 410° C. in nitrogen and 390° C. in air, respectively, when heated at 20° C./minute.

EXAMPLE 7

Copolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ with Perfluoro-2,2-dimethyl-1,3-dioxole (PDD)

A 25 mL glass ampul fitted with a Teflon® coated stir bar was charged with 0.01 mL of 5% of bis(perfluoropropionyl) peroxide in 1,1,2-trichlorotri-fluoroethane and 0.65 g of the title compounds and 0.8 g of PDD. The ampul was sealed and cooled in a liquid nitrogen bath. After being evacuated and purged with $N_2$ alternately six times, contents of the sealed ampul were stirred at 40° C. overnight. White solids was washed with ethyl acetate and dried under vacuum at 100° C. to give 0.86 g of polymer. The polymer had a glass transition temperature of 139.1 ° C. and no melting point by DSC (second heat). By TGA the polymer showed a 10% weight loss temperature of about 470° C. in air when heated at 200° C./minute.

EXAMPLE 8

Copolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ with Chlorotrifluoroethylene A 25 mL glass ampul fitted with a Teflon® coated stir bar was charged with 0.01 mL of 5% of bis(perfluoropropionyl) peroxide in 1,1,2-trichlorotrifluoroethane and 0.65 g of the title compounds and 1.0 g of chlorotrifluoro-ethylene. The ampul was sealed and cooled in a liquid nitrogen bath. After being evacuated and purged with $N_2$ alternately six times, contents of the sealed ampul were stirred at 40° C. overnight. White solids was washed with ethyl acetate and dried under vacuum at 100° C. to give 0.52 g of polymer. The polymer had a glass transition temperature of 127° C. and no melting point by DSC (second heat). By TGA the polymer showed a 10% weight loss temperature of about 385° C. in nitrogen when heated at 20° C./minute.

EXAMPLE 9

Copolymerization of a Mixture of 94 to 6 Ratio of $CF_2=CFCF_2CF(CF_3)CH_2CH=CH_2$ and $CF_2=CFCF(CF_3)CF_2CH_2CH=CH_2$ with $CF_2=CFOCF_2CF(CF_3)OCF_2CF_2SO_2F$ (PSEPVE)

A 25 mL glass ampul fitted with a Teflon® coated stir bar was charged with 0.01 mL of 5% of bis(perfluoropropionyl) peroxide in 1,1,2-trichlorotri-fluoroethane and 0.65 g of the title compounds and 0.85 g of PSEPVE. The ampul was sealed and cooled in a liquid nitrogen bath. After being evacuated and purged with $N_2$ alternately six times, contents of the sealed ampul were stirred at 40° C. overnight. The white solid was washed with ethyl acetate and dried under vacuum at 100° C. to give 0.60 g of polymer. The polymer had glass transition temperatures of 127.6° C., 190.3° C. and 364° C. and no melting point by DSC (second heat). By TGA the polymer showed a 10% weight loss temperature of about 400° C. in nitrogen when heated at 20° C./minute.

What is claimed is:

1. A compound of the formula $CF_2=CFCF_2CF(CF_3)CH_2CH=CH_2$ or $CF_2=CFCF(CF_3)CF_2CH_2CH=CH_2$.

2. The compound as recited in claim 1 of the formula $CF_2=CFCF_2CF(CF_3)CH_2CH=CH_2$.

3. The compound as recited in claim 1 of the formula $CF_2=CFCF(CF_3)CF_2CH_2CH=CH_2$.

* * * * *